United States Patent [19]

Telschow

[11] Patent Number: 4,571,432

[45] Date of Patent: Feb. 18, 1986

[54] PREPARATION OF CINNAMIC ACID

[75] Inventor: Jeffrey E. Telschow, Tarrytown, N.Y.

[73] Assignee: Stauffer Chemical Company, Westport, Conn.

[21] Appl. No.: 685,353

[22] Filed: Dec. 24, 1984

[51] Int. Cl.$^4$ ............................................. C07C 63/64
[52] U.S. Cl. ................................................... 562/495
[58] Field of Search ......................................... 562/495

[56] References Cited

U.S. PATENT DOCUMENTS

| | | | |
|---|---|---|---|
| 2,370,067 | 5/1945 | Long | 562/495 |
| 2,918,494 | 12/1959 | Closson | 562/495 |
| 3,870,751 | 3/1975 | Houlihan et al. | 562/495 |
| 4,433,160 | 2/1984 | Amano et al. | 562/495 |

FOREIGN PATENT DOCUMENTS

| | | | |
|---|---|---|---|
| 17467 | 8/1895 | Fed. Rep. of Germany | 562/495 |
| 81830 | 11/1973 | Japan | 562/495 |

OTHER PUBLICATIONS

Kirk Othmer, Encyclopedia of Chem. Technology, 3rd Ed., vol. 6, pp. 142–149, 1981.

*Primary Examiner*—Paul J. Killos

[57] ABSTRACT

A process for the production of cinnamic acid is disclosed. The process uses an inert diluent to increase the stirrability of the reaction mixture and uses an amine derivative as a catalyst. The present process also uses combinations of acetic acid derivatives to produce the cinnamic acid.

15 Claims, No Drawings

PREPARATION OF CINNAMIC ACID

FIELD OF THE INVENTION

The present invention relates to an improved process for the production of cinnamic acid.

BACKGROUND OF THE INVENTION

Cinnamic acid, or 3-phenyl-2-propenoic acid, is an important industrial chemical. Cinnamic acid and its derivatives are used as sun screening agents, flame retardants, cosmetics, fungicides, insecticides, food preservatives, pharmaceuticals and photographic agents. Cinnamic acid has also received considerable attention recently since it is a precursor of phenylalanine, one of the ingredients in the artificial sweetener aspartame.

The most widely used commercial process for the production of cinnamic acid has used benzaldehyde, acetic anhydride and anhydrous sodium or potassium acetate in a Perkin condensation reaction. In another commercial process for the production of cinnamic acid, benzal chloride and anhydrous sodium acetate are heated to 180° to 200° C. Since benzal chloride is cheaper than benzaldehyde, this method is especially favored by manufacturers who obtain by-product benzal chloride from their benzyl chloride plants. This basic reaction, disclosed in German Pat. Nos. 17467 and 18251, required severe reaction conditions, namely 20 atmospheres pressure and temperatures above 200° C. for 10–20 hours. These severe reaction conditions are undesirable due to the attendant dangers associated with high pressure as well as for economic reasons. Furthermore, large quantities of a tarry component are produced under the above reaction conditions.

An improvement in the above described process is reported in Japanese Pat. No. 48-81830 (1973) wherein the inventors in this Japanese application disclose that potassium acetate can be reacted with benzal chloride under normal pressure to produce high yields of cinnamic acid if an amine such as pyridine, quinoline or aniline is used as a catalyst. The process reported in the above Japanese patent is not easily reproducible. Present attempts to reproduce the results reported in this patent have resulted in yields of cinnamic acid significantly lower than those reported by the Japanese inventors. Moreover, under the conditions reported in the above patent, a difficultly stirrable reaction mixture is produced. In the process disclosed in the above Japanese patent, the preferred amount of potassium acetate is 4–5 moles per mole of benzal chloride. The Japanese inventors disclose that 3 moles can be used but regardless of the molar amount of potassium acetate used, the above process still requires the use of large amounts of the expensive potassium salt for the desired yields.

The use of condensing agents in Friedel-Crafts synthesis is also well documented. A complete discussion of this subject can be found in the article entitled "The Friedel-Crafts Synthesis", Chem. Rev. 17, p. 376, 1936.

SUMMARY OF THE INVENTION

In accordance with the present invention, it has now surprisingly been found that the yield of cinnamic acid produced when an acetic acid derivative is allowed to react with a halogenated benzal derivative is increased when an inert diluent is added to the reaction mixture.

In another embodiment of the present invention, it has also been found that other amine catalysts may be used in the above reaction.

In yet another embodiment of the present invention, a process for the production of cinnamic acid is disclosed wherein combinations of acetic acid derivatives may be used.

DETAILED DESCRIPTION OF THE INVENTION

The present invention relates to a process for manufacturing cinnamic acid and/or salts thereof from a halogenated benzal derivative and an acetic acid derivative. The above reaction can be expressed as follows:

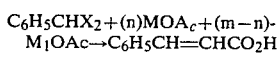

wherein X is halogen, i.e. Cl, Br or I, M and $M_1$ are the same or different and are alkali metals and m and n are integers from 0–3.

In one embodiment of the invention, the halogenated benzal derivative and the acetic acid derivative are reacted together in the presence of an amine catalyst. To improve the stirrability of the reaction, an inert diluent is added to the reaction mixture.

The halogenated benzal derivative is chosen from the group consisting of benzal chloride, benzal iodide and benzal bromide. The preferred compound is benzal chloride.

The halogenated benzal derivative can in addition be ring substituted with additional sterically compatible groups which are non-reactive under the conditions of the reaction such as chloro, fluoro, nitro, cyano, alkyl, alkoxy, alkylthio, aryl, alkyl substituted aryl, alkoxy substituted aryl, or aryloxy. Thus, when the above ring substituted halogenated benzal derivative is used in the reaction of the present invention, a ring substituted cinnamic acid would be produced.

The term "acetic acid derivative" includes acetic acid as well as salts of acetic acid, sodium acetate, potassium acetate or other acetic acid derivatives. The molar ratio of the reactants used can range from about 2 to about 5 moles of the acetic acid derivative per mole of the halogenated benzal derivative. In an especially preferred embodiment of the invention, the sodium and potassium salts of acetic acid are used in a 2 moles sodium acetate/1 mole potassium acetate ratio. Thus, the reaction is run at a 3 mole salt of acetic acid derivative/1 mole halogenated benzal derivative ratio. Hereinafter, by the term "acetic acid derivative" is meant either a single salt or combinations of salts of acetic acid.

The catalyst used in the reaction can be any conventional catalyst reported in the literature to which this invention pertains. Preferred catalysts are amines such as pyridine, quinoline and aniline. Especially preferred amine catalysts are tetramethylethylenediamine, hereinafter called TMEDA, and 4-dimethylaminopyridine. The amount of catalyst can range from about 2 to about 10 percent by weight of the halogenated benzal derivative.

Inert diluents used in the present invention include any liquid which has a boiling point high enough to permit the desired reaction to occur and is non-reactive under the reaction conditions used. Examples of inert diluents include mineral oil, Tetralin ® diluent, 2-ethoxyethyl ether, and high boiling hydrocarbons. The amount of inert diluent used is not critical and amounts ranging from about 0.5 to about 5 milliliters of diluent per milliliter of reaction mixture can be used.

The temperature at which the reaction is carried out can range from about 145° to about 210° C. An especially preferred temperature at which the process of the present invention is carried out is about 180° C.

The reaction time can range from about 5 to about 40 hours. A preferred reaction time for the process of the present invention is about 17 hours.

The order in which the reactants are added is not critical. The halogenated benzal derivative, acetic acid derivative and catalyst can be added to the inert diluent or the inert diluent can be added to mixture of the halogenated benzal derivative, catalyst, and acetic acid derivative.

The process of the present invention is carried out in an inert atmosphere such as nitrogen.

The stirring of the reaction mixture can be accomplished by using a mechanical stirrer.

At the conclusion of the reaction, usually after about 15-20 hours, the cinnamic acid, ring-substituted cinnamic acid, and/or salt form thereof, remains in the thick mixture. The mixture is then diluted with water and basified using a known amount of caustic. The basified solution is separated and then acidified with a known amount of hydrochloric acid. Conventional extraction, filtering and washing techniques well known to those skilled in the art are then used to purify the desired product.

The present invention is illustrated by the following non-limiting examples.

COMPARISON EXAMPLE 1

This example shows the effect of using pyridine as a catalyst without the addition of an inert diluent. The procedure is essentially that of Japanese Pat. No. 48-81830 (1973).

To 40 grams (0.4 mole) of anhydrous potassium acetate in a 250 milliliter 3-necked flask under nitrogen were added 16.1 grams (0.10 mole) of benzal chloride and 0.5 milliliter of pyridine. The mixture formed was heated in a 190° C. oil bath with slow stirring. Even with this slow stirring, solids collected on the upper walls of the flask and a large amount of a brown solid moved about on the stirrer shaft. The mixture was heated for 18 hours.

At the end of this time, the stirrability of the brown solid had improved somewhat and none stuck to the side of the flask. A colorless distillate was refluxing gently. The temperature of the reaction mixture when the stirring was stopped was approximately 175° C. A 30 milliliter portion of $H_2O$ was added after cooling somewhat and steam distillation began with bath temperature about 150°. More $H_2O$ was added at intervals up to about 70 milliliters. When little unreacted benzal chloride could be seen co-distilling with the $H_2O$, the distillation was stopped. Large amounts of a brown material were seen suspended in the $H_2O$. Another 30 milliliters of $H_2O$ was added but this material did not go into solution.

The mixture was filtered while still warm and the filtrate was colorless and crystallized. The pH was about 5 so it was acidified with 6N HCl to pH 2.

The aqueous layer was extracted twice with $CHCl_3$, dried with $MgSO_4$ and evaporated. Light yellow crystals with a melting point of from 105° C. to about 123° C. were obtained.

The filtered solid did partially dissolve in hot NaOH. The basic washes were then acidified with 6N HCl and another 4.5 grams of faint yellow crystals were produced. Melting point of the crystals was 130°–131° C. The total yield was 36.5 percent.

COMPARISON EXAMPLE 2

The procedure was essentially that of Comparison Example 1, i.e. that of Japanese Pat. No. 48-81830 (1973), except sodium acetate, in the same molar proportions, was substituted for potassium acetate.

The reaction was carried out under nitrogen for 18 hours and at the end of the reaction, a total of 100 milliliters of water was added to the cool solid to aid in distillation. The reaction mixture contained a nearly colorless solution with small amounts of brownish and whitish suspended solids. A total of 20.9 grams of NaOH was added to bring the solution to pH 11 but the suspended solids did not go into solution. An additional 50 milliliters of water was added but the solids still did not go into solution. After repeated filterings, a yellow curdy solid was obtained. This solid was then acidified with 6N HCl, filtered, dried and extracted. The solid phase yielded light tan crystals with a m.p. 129°–137° C. The yield was 17 percent.

EXAMPLE 1

This example shows the effect of using a diluent to increase stirrability.

To a 250 milliliter, 3 necked flask were added 16.1 grams (0.1 mole) of benzal chloride, 40 grams (0.4 mole) of anhydrous potassium acetate, 0.5 milliliter of pyridine and 20 milliliters of Tetralin ® diluent (1,2,3,4 tetrahydronapthalene, Aldrich Co.). Faster stirring could be used since the samples did not stick to the walls of the reaction vessel.

The reaction mixture was heated in a 190° C. oil bath. After 16 hours, the temperature of the reaction mixture was 175° C. and the solids had curded. The color of the reaction mixture was light brown. One hundred milliliters of water was added to the reaction mixture. At this point, a top dark brown organic layer and a bottom, colorless aqueous layer, was seen. The heating was stopped and the reaction mixture was basified to pH 11.0 with 14.0 grams of 50 percent NaOH. Solids began to fall out in the organic phase. The aqueous phase was decanted into an Erlemeyer flask wherein, upon cooling, it solidified into a white solid.

To the organic phase was added 50 milliliters of water and the mixture was reheated until all the solids had gone into solution.

The aqueous phase was separated, combined with the other aqueous layer and the pH was adjusted to 1.0 with concentrated HCl. The reaction mixture was extracted twice with 25 milliliters of chloroform at which point all solids went into solution. The pale yellow organic layers were combined and stipped on a rotary evaporator to dryness and then placed under a high vacuum. A light yellow solid with a melting point of 125° to 130° C. was obtained. The yield of cinnamic acid was 45 percent.

EXAMPLE 2

The procedure was essentially that of Example 1 except a larger amount (2.0 milliliter) of pyridine was used.

After basification followed by acidification of the reaction mixture and then final extraction procedures, a light yellow solid with a melting point of 124° to 129° C. at a yield of 30 percent was obtained.

EXAMPLE 3

Similar to Example 1 except 1.0 milliliter of pyridine was used. After workup of the final product, a light yellow solid having a melting point of 124°-129° C. was obtained. Final yield of the product was 44.5 percent.

EXAMPLES 4-5

Similar to Example 1 except two identical reaction mixtures A and B were set up. Reaction A was reacted for 1 day and reaction B was reacted for 2 days. Reaction A gave a 32 percent yield. Reaction B gave a 30 percent yield.

EXAMPLE 6

Similar to Example 1 except 2-ethoxyethyl ether was used as a diluent. After extraction and washing procedures, a 55 percent yield of cinnamic acid was obtained.

EXAMPLE 7

This example illustrates the use of N,N,N',N'-tetramethylethylenediamine as a catalyst and mineral oil as a diluent.

To a 250 milliliter, 3 necked flask were added 19.4 milliliters (0.15 mole) of benzal chloride, 44.0 grams (0.45 mole) of potassium acetate, 30 milliliters of Kaydol® mineral oil as a diluent and 1 milliliter of N,N,N',N'-tetramethylethylenediamine (J. T. Baker Co. hereinafter called TMEDA) as a catalyst. The reaction was carried out under nitrogen with the reaction vessel in a 200° C. oil bath. An additional 10 milliliters of mineral oil was added to increase stirrability. The mixture was heated for 17 hours.

At the end of the heating period, a total of 110 milliliters of water was added to aid in the solubility of the solids formed. A two phase mixture was formed. The mixture was then basified with 50 percent NaOH to a pH of ~10. The phases were separated and the aqueous phase was acidified with concentrated HCl. After extraction, drying and washing, 14.0 grams of light tan crystals with a melting point of 114°-120° C. were obtained. Total yield was 63 percent.

EXAMPLE 8

This example illustrates the use of pyridine as a catalyst and mineral oil as a diluent. To a 250 milliliter, 3 necked reaction vesel were added 96.7 grams (0.60 mole) of benzal chloride, 17.7 grams (1.80 mole) of potassium acetate, 4 milliliters of pyridine and 120 milliliters of mineral oil. The reaction was carried out under nitrogen gas with the reaction vessel in an oil bath at about 200° C.

After about 15 minutes of heating, 25 milliliters of mineral oil was added and then 20 milliliter increments were added over a 1 hour period. The total amount of mineral oil added was 295 milliliters.

After 20 hours of heating, a total of 600 milliliters of water was added to the reaction mixture. The reaction mixture, now in two phases, was then basified with 50 percent sodium hydroxide and kept hot to prevent precipitation of sodium cinnamate. The separated aqueous phase was acidified to pH 1 with 6N HCl. After washing, extracting and drying, the yield of the final product was 35 percent.

EXAMPLE 9

This example shows that a 2 mole potassium acetate/1 mole sodium acetate ratio can be used when pyridine is used as the catalyst and mineral oil is used as the inert diluent.

The procedure was essentially that of Example 8 except 14.4 milliliters (0.15 mole) of benzal chloride, 29.3 grams (0.30 mole) of potassium acetate, 14.7 grams (0.17 mole) of sodium acetate, 1.0 mililliter of pyridine as a catalyst and 50 milliliters of mineral oil as a diluent were used. The final yield was 34 percent.

EXAMPLE 10

This example illustrates that the potassium acetate/sodium acetate ratio can be lowered to 1:2 when TMEDA is used as a catalyst and mineral oil is used as a diluent.

To a 1 liter, 3 necked reaction vessel fitted with a condenser, nitrogen source and stirring mechanism were added 80.5 grams (0.5 mole) of benzal chloride, 49 grams (0.5 mole) of anhydrous potassium acetate, 82 grams (1.0 mole) of anhydrous sodium acetate, 2.6 milliliters of TMEDA as a catalyst and 230 milliliters of mineral oil as a diluent. The reaction mixture was heated to 175° C. to 180° C. for 22 hours.

Three hundred and fifty milliliters of water was then added to the reaction mixture. The mixture was basified to pH 10 with 50% NaOH. An additional 100 milliliters of water was then added. The solution was heated slightly, the aqueous layer was siphoned off, and an additional 350 milliliters of water was added. The newly formed aqueous layer was combined with the previously collected aqueous layer. The aqueous layers were then acidified to pH 1 with 6N HCl. After extracting, washing and drying, a solid having a melting point of 128°-129.5° C. was obtained. Final yield was 60.8 percent.

NOTES ON EXAMPLES

The acetic acid derivative used in the above examples should be as anhydrous as possible. Either a commercially available anhydrous product (Aldrich Co.) can be used or the acetic acid salts used can be dried at 250° C. and weighed in a dry box.

The temperature of the aqueous phase should be kept near 100° C. to prevent precipitation of the cinnamate salt prior to the separation of layers during workup.

At the conclusion of the reaction, the cinnamic acid may be present in either the acid form or the salt form.

The preferred and most preferred embodiments of the present invention are found in the claims hereinafter.

What is claimed is:

1. A process for the production of cinnamic acid, a ring-substituted cinnamic acid, and salts thereof from a halogenated benzal derivative and acetic acid derivative which comprises carrying out the reaction in the presence of an amine catalyst and adding an inert diluent, said inert diluent increasing the stirrability of the reaction mixture.

2. A process according to claim 1 wherein the temperature is from about 145° C. to about 210° C.

3. A process according to claim 1 wherein said halogenated benzal derivative is benzal chloride, benzal iodide or benzal bromide.

4. A process according to claim 3 wherein said halogenated benzal derivative is benzal chloride.

5. A process according to claim 1 wherein said halogenated benzal derivative is used in a 1:3 ratio of halogenated benzal derivative to acetic acid derivative.

6. A process according to claim 1 wherein said acetic acid derivative is an alkali metal derivative of acetic acid.

7. A process according to claim 6 wherein said alkali metal derivative of acetic acid comprises sodium acetate and potassium acetate in a 2:1 ratio.

8. A process according to claim 1 wherein said amine catalyst is pyridine, N,N,N',N'-tetramethylethylene diamine or 4-dimethylaminopyridine.

9. A process according to claim 8 wherein said amine catalyst is pyridine.

10. A process according to claim 8 wherein said amine catalyst is N,N,N',N' tetramethylethylenediamine.

11. A process according to claim 1 wherein said inert diluent is tetralin, decalin or mineral oil.

12. A process according to claim 11 wherein said inert diluent is tetralin.

13. A process according to claim 11 wherein said inert diluent is decalin.

14. A process according to claim 11 wherein said inert diluent is mineral oil.

15. A process according to claim 1 wherein said inert diluent is 2-ethoxyethyl ether.

* * * * *

UNITED STATES PATENT AND TRADEMARK OFFICE
CERTIFICATE OF CORRECTION

PATENT NO. : 4,571,432
DATED : Feb. 18, 1986
INVENTOR(S) : Jeffrey E. Telschow

It is certified that error appears in the above—identified patent and that said Letters Patent is hereby corrected as shown below:

Col. 3, line 13, "to mixture" should read --to a mixture--;

Col. 4, line 34, "tetrahydronapthalene" should read --tetrahydronaphthalene--;

Col. 4, line 57, "stipped" should read --stripped--;

Col. 5, line 50, "vesel" should read --vessel--;

Col. 6, line 10, mililliter" should read --milliliter--; and

Col. 8, line 2 (claim 10, line 2), a hyphen should appear after "N,N,N',N'".

Signed and Sealed this

Twentieth Day of May 1986

[SEAL]

Attest:

DONALD J. QUIGG

Attesting Officer

Commissioner of Patents and Trademarks